US012805665B2

(12) United States Patent
Van Erp

(10) Patent No.: US 12,805,665 B2
(45) **Date of Patent: *Nov. 24, 2026**

(54) FRYING OIL SENSING MEANS AND FRYING OIL MANAGEMENT WITHIN AN INDUSTRIAL FRYER SETUP

(71) Applicant: GEA FOOD SOLUTIONS BAKEL B.V., Bakel (NL)

(72) Inventor: Joost Van Erp, Nuenen (NL)

(73) Assignee: GEA FOOD SOLUTIONS BAKEL B.V., Bakel (NL)

( * ) Notice: Subject to any disclaimer, the term of this patent is extended or adjusted under 35 U.S.C. 154(b) by 290 days.

This patent is subject to a terminal disclaimer.

(21) Appl. No.: 18/570,280

(22) PCT Filed: Jul. 5, 2022

(86) PCT No.: PCT/EP2022/068587

§ 371 (c)(1),
(2) Date: Dec. 14, 2023

(87) PCT Pub. No.: WO2023/280852

PCT Pub. Date: Jan. 12, 2023

(65) Prior Publication Data

US 2024/0288383 A1 Aug. 29, 2024

(30) Foreign Application Priority Data

Jul. 7, 2021 (EP) .................................... 21184156

(51) Int. Cl.
*A47J 37/12* (2006.01)
*A23L 5/10* (2016.01)
(Continued)

(52) U.S. Cl.
CPC ............ *A47J 37/1266* (2013.01); *A23L 5/11* (2016.08); *A47J 37/1214* (2013.01);
(Continued)

(58) Field of Classification Search
None
See application file for complete search history.

(56) References Cited

U.S. PATENT DOCUMENTS

| | | | |
|---|---|---|---|
| 7,334,451 | B1 | 2/2008 | Fauveau |
| 2005/0153022 | A1 | 7/2005 | Schilling et al. |

(Continued)

FOREIGN PATENT DOCUMENTS

| | | | |
|---|---|---|---|
| CN | 104271017 | A | 1/2015 |
| WO | 2020/139952 | A1 | 7/2020 |
| WO | 2020/191150 | A1 | 9/2020 |
| WO | 2020/193615 | A1 | 10/2020 |
| WO | 2021/028130 | A1 | 2/2021 |

OTHER PUBLICATIONS

Extended European Search Report for EP 25179896.3-1105 / 4585909, dated Sep. 12, 2025.

(Continued)

*Primary Examiner* — John J Norton
(74) *Attorney, Agent, or Firm* — The Dobrusin Law Firm, P.C.

(57) ABSTRACT

A fryer for frying food products that includes a frying vessel for accommodating a frying oil, a guided wave radar sensor arranged in the frying vessel, and an analysis unit for determining a permittivity of the frying oil in the frying vessel based on measurement data of the guided wave radar sensor, the fryer is configured for continuously frying food products and comprises at least one conveyor for conveying the food products to be fried through the frying vessel.

15 Claims, 4 Drawing Sheets

(51) Int. Cl.

| | |
|---|---|
| ***G01F 23/284*** | (2006.01) |
| ***G01N 21/25*** | (2006.01) |
| ***G01N 22/00*** | (2006.01) |
| ***G01N 22/04*** | (2006.01) |
| ***G01N 33/03*** | (2006.01) |

(52) U.S. Cl.

CPC ........ *A47J 37/1223* (2013.01); *G01F 23/284* (2013.01); *G01N 21/25* (2013.01); *G01N 22/00* (2013.01); *G01N 22/04* (2013.01); *G01N 33/03* (2013.01); *A47J 2202/00* (2013.01); *A47J 2203/00* (2013.01)

(56) References Cited

U.S. PATENT DOCUMENTS

| | | | | |
|---|---|---|---|---|
| 2011/0214502 | A1* | 9/2011 | Zhang | G01F 23/2845 73/290 V |
| 2011/0246100 | A1* | 10/2011 | Carvalho | G01F 23/284 702/50 |
| 2015/0027205 | A1* | 1/2015 | Brugger | G01N 27/00 99/403 |
| 2016/0033463 | A1 | 2/2016 | Robertson et al. | |
| 2018/0035696 | A1* | 2/2018 | Bartlett | A21C 1/1425 |
| 2019/0310125 | A1* | 10/2019 | Farmanyan | G01S 13/106 |
| 2021/0186266 | A1 | 6/2021 | Tirumala et al. | |
| 2022/0218150 | A1 | 7/2022 | Van Gerwen | |
| 2022/0283210 | A1 | 9/2022 | Blödt | |
| 2024/0125714 | A1* | 4/2024 | Barr | G01N 1/20 |

OTHER PUBLICATIONS

Extended European Search Report for EP 25179142.2-1105 / 4585908, dated Sep. 12, 2025.

Chinese First Office Action Issued Nov. 28, 2025, for Chinese patent application No. 202280047149.8.

Venkatesh; An Overview of Dielectric Properties Measuring Techniques https://www.researchgate.net/publication/235435108_An_Overviewof_Dielectric_Properties_Measuring_Techniques p. 7.10-p. 7.20 (2005).

Technical Note Contents; Guided Wave Radar Interface Measurement https://web.archive.org/web/20220127210054/https://www.emerson.com/documents/automation/technical-not-guided-wave-radar-interface-measurement-rosemont-en-78542.pdf (Oct. 2014).

International Search Report and Written Opinion dated Dec. 12, 2022, for International Application PCT/EP2022/068587.

International Preliminary Report on Patentability dated Sep. 29, 2023, for International Application PCT/EP2022/068587.

USPTO Office Action for U.S. Appl. No. 18/570,252 mailed on Jun. 2, 2026.

Chinese Office Action for CN Application No. 202280047149.8 Issued on May 21, 2026, by the Chinese Patent Office.

Research on Oil-Water Interface Measurement Technology Based on TDR by Zhang Lijuan completed on Mar. 28, 2014, from China Excellent Master's Degree Theses Full-text Database—Engineering Science & Technology I (Monthly), 2020, Issue 04 (Published Mar. 16, 2020 to Apr. 15, 2020) and published by China Academic Journals (CD-ROM) Electronic Magazine Society ISSN: 1674-0246.

* cited by examiner

FRYING OIL SENSING MEANS AND FRYING OIL MANAGEMENT WITHIN AN INDUSTRIAL FRYER SETUP

CROSS-REFERENCE TO RELATED APPLICATIONS

This application is a US National Stage of PCT/EP2022/068587 filed on Jul. 5, 2022, which claims priority to EP 21184156.4 filed on Jul. 7, 2021.

FIELD

The present invention relates to the field of frying of food products, in particular on an industrial scale. Specifically, the invention relates to a fryer for frying food products comprising a frying vessel for accommodating a frying oil. The invention further relates to a method for frying food products in a frying vessel of a fryer, wherein the frying vessel contains a frying oil or melted frying fat.

BACKGROUND

The process of frying includes cooking of food products partly submerged (shallow-frying) or entirely submerged (deep-frying) in a frying oil and/or molten frying fat at high temperatures, in particular in the range of 180 to 190° C. Industry scale fryers typically comprise a conveyor that conveys the food products to be fried through the frying vessel that contains the frying oil. During use, frying oils undergo changes in their chemical composition. In its fresh state, the frying oil does not comprise substantial amounts of polar materials. With continued use of the frying oil, the oil decomposes and the amount of polar materials increases. When the amount of total polar materials (TPM) reaches the range of 24% to 27%, the frying oil is not considered to be suitable for consumption and should therefore be replaced or freshened with replacement frying oil.

The amount of total polar materials can be determined by capacitive measurement, thus, by measuring the capacitance of a capacitor that is submerged in the frying oil. Capacitive measuring instruments for determining TPM in kitchen fryers are available on the market. One of those instruments is the testo 270 cooking oil tester as offered by TESTO SE & CO. KGAA.

A similar measurement technique is known from WO 2020/191 150 A1 that discloses a batch fryer for use in a kitchen. An oil caddy is provided that can be attached to the batch fryer to receive oil exiting a frying vat of the batch fryer. The oil caddy includes a sensor for measuring the capacitance of the oil whereas an oil quality is derived from the measured capacitance in terms of total polar materials (TPM) present in the oil.

SUMMARY

In light of the above, it is an object of the present invention to enable determining the quality of frying oil used in industrial scale fryers.

To better address this concern, in a first aspect of the invention a fryer for frying food products is presented, comprising a frying vessel and optionally a chamber, in particular a pump chamber, which is part of the frying vessel or which is fluidly connected to the frying vessel for accommodating a frying oil, further comprising a guided wave radar sensor for determining a permittivity of the frying oil accommodated in the frying vessel and/or the chamber based on measurement data of the guided wave radar sensor.

According to another aspect of the invention, a food processing line is presented which includes a fryer for frying food products, comprising a frying vessel for accommodating a frying oil, further comprising a guided wave radar sensor for determining a permittivity of the frying oil accommodated in the frying vessel based on measurement data of the guided wave radar sensor.

According to yet another aspect of the invention, a method for frying food products in a frying vessel of a fryer is presented, wherein the frying vessel contains frying oil or melted frying fat, in particular wherein at least one conveyor conveys the food products to be fried through the frying vessel, wherein an analysis unit determines a permittivity of the frying oil accommodated in the frying vessel or in a chamber that is part of the frying vessel or in a chamber that is fluidly connected to the frying vessel based on measurement data of a guided wave radar sensor.

The guided wave radar sensor enables determining the permittivity of the frying oil in the frying vessel. Based on the determined permittivity, the quality of the frying oil in the frying vessel may be determined. The guided wave radar sensor further enables in-line real-time determination of permittivity, whereby the processing of food products in industrial scale fryers may be improved.

As compared to conductive and/or capacitive sensors, the guided wave radar sensor not only enables inline measurements but also allows to carry out reliable measurements of permittivity of the frying oil in a wide range of temperatures, e.g., temperatures in the range of 0° C. to 190° C., in particular in the range of 0° C. to 180° C. The guided wave radar sensor will not be influenced by dirt floating in the frying oil, e.g., burned crumb.

According to the invention, the frying vessel may contain a frying oil. The frying oil may be used for frying the food products in the frying vessel. Alternatively, frying vessel may contain residues or parts of pure water or a composition comprising water and a cleaning agent or a composition comprising water and impurities, e.g., fat, oil or dirt. Water may be accommodated in the frying vessel for cleaning the frying vessel.

According to the invention, the analysis unit may be part of a control system of the fryer and/or may be a unit separate from the control system of the fryer and/or may be part of the control system of a food processing line the fryer is part of and/or may be part of a centralized control system and/or maybe be part of the guided wave radar sensor. The analysis unit may comprise a processor, in particular a programmable processor.

The guided wave radar sensor may comprise a radar transmitter for generating a signal, a waveguide coupled to the radar transmitter for guiding the wave towards and/or through the frying oil and/or a radar receiver for receiving waves reflected by the frying oil and/or a wall of the vessel. The guided wave radar sensor, in particular the waveguide of the guided wave radar sensor, may partially be arranged within the frying oil. The waveguide may be constructed of metal, in particular steel. The waveguide may have the form of a rod or a rope. For example, an end tip of the guided wave radar sensor, in particular the waveguide of the guided wave radar sensor, may be submerged in the frying oil. The guided wave radar sensor is preferably configured to measure time of flight of signals sent by the transmitter over the waveguide and received by the receiver after being reflected by the frying oil and/or a wall of the vessel.

According to a preferred embodiment of the invention, the guided wave radar sensor comprises a stilling well. The stilling well may be implemented as a stilling pipe. The stilling well may surround the waveguide of the guided wave radar sensor so as to reduce influence of disturbances such as flow of the frying oil, impurities in the frying oil, surrounding structures and mechanical impact. Preferably, the stilling well comprises one or more openings through which frying oil may flow from the outside of the stilling well to the inside, and vice versa. The one or more openings may be arranged in a shell surface of the stilling well.

According to a preferred embodiment of the invention, the fryer is configured for continuously frying food products and comprises at least one conveyor for conveying food products to be fried through the frying vessel. The conveyor is preferably configured for conveying food products from a product entry of the fryer to a product exit of the fryer. The conveyer may comprise a belt, in particular an endless belt. The belt may be implemented as a mesh belt so as to allow flow of frying oil through the belt. The fryer may additionally comprise a submerge conveyor that hinders the products from floating to the fluid level of the frying oil. The submerge conveyor may comprise a belt, in particular an endless belt. The belt may be implemented as a mesh belt so as to allow flow of frying oil through the belt. The submerge conveyor is preferably arranged above the conveyor.

According to a preferred embodiment of the invention, the guided wave radar sensor is arranged in the frying vessel. Thereby, the quality of the frying oil may be determined directly at the place the frying process takes place.

According to a particularly preferred embodiment of the invention, the guided wave radar sensor is arranged in a pump chamber which is part of the frying vessel. The pump chamber comprises a pump which serves to circulate frying oil within the fryer. Preferably, the pump chamber and the frying vessel are fluidly connected as communicating vessels so the frying oil at the pump chamber and the frying oil in the frying vessel balance out at the same level.

According to a further preferred embodiment of the invention at least one additional guided wave radar sensor is arranged in a storage tank for frying oil. One or more storage tanks can be fluidly connected to the fryer in order to store frying oil. For instance, one storage tank comprises a first type of replacement oil (fresh oil), another storage tank comprises a second type of replacement oil (frying oil which is still usable) and another storage tank comprises frying oil which cannot be used anymore, for instance due to a too high percentage of TPM. Preferably each and every storage tank comprise an additional guided wave radar sensor for determining the permittivity of the frying oil in the respective storage tank. Preferably each and every storage tank comprises valves and/or pumps which are connected to the fryer in order to fill/empty the storage tanks. Preferably, the analysis unit is further configured to determine a permittivity of the frying oil in the respective storage tanks based on measurement data of the additional guided wave radar sensor(s) arranged in the storage tank(s).

According to a further preferred embodiment of the invention at least one additional guided wave radar sensor is arranged in the piping fluidly connecting the frying vessel and the at least one storage tank, preferably multiple storage tanks. By means of the additional guided wave radar sensor in the piping, frying oil can be detected in the piping. This may be helpful in case frying oil is drained from the frying vessel. Thereby, it may be prevented that frying oil remains in the piping after emptying the frying vessel and mixes with cleaning water in a subsequent cleaning step. Further, it may be prevented if cleaning water is removed from the piping before filling the frying vessel with frying oil after the cleaning step has been finished. Thus, unwanted mixing of frying oil and cleaning water can be avoided. The additional guided wave radar sensor arranged in the piping can also be used to determine if cleaning agents remain in the piping, so as to decide if a (further) rinsing step is required to remove all cleaning agents from the piping.

Preferably, the control unit is configured to control the inflow of replacement frying oil into the frying vessel, preferably from the at least one storage tank that is arranged in fluid communication with the frying vessel; and/or the outflow of used frying oil from the frying vessel, preferably to the at least one storage tank that is arranged in fluid communication with the frying vessel additionally based on the measurements of the at least one additional guided wave radar sensor which is arranged in the storage tank and/or the at least one additional guided wave radar sensor which is arranged in the piping.

According to a preferred embodiment of the invention, the analysis unit is configured to determine the permittivity of the frying oil in the vessel based on measurement data of the guided wave radar sensor associated with a signal reflection at an interface between air and the frying oil. The method according to the invention preferably includes that the analysis unit determines the permittivity of the frying oil in the vessel based on measurement data of the guided wave radar sensor associated with a signal reflection at an interface between air and the frying oil. In particular, the permittivity of the frying oil is determined as a function of an amplitude of the signal reflected at the interface between air and frying oil. Preferably, a stronger reflected signal relates to a higher permittivity of the frying oil.

According to a preferred embodiment of the invention, the analysis unit is configured to determine an amount of total polar material of the frying oil in the vessel and/or an amount of free fatty acids in the frying oil in the vessel depending on the determined permittivity, in particular at a certain oil temperature. The method according to the invention preferably includes that the analysis unit determines an amount of total polar material of the frying oil in the vessel and/or an amount of free fatty acids in the frying oil in the vessel depending on the determined permittivity.

According to a preferred embodiment of the invention, the analysis unit is configured to determine the amount of total polar material of the frying oil in the vessel and/or the amount of free fatty acids in the frying oil in the vessel additionally depending on predetermined calibration data. In the method according to the invention, it is preferred that the analysis unit determines the amount of total polar material of the frying oil in the vessel and/or the amount of free fatty acids in the frying oil in the vessel additionally depending on predetermined calibration data. The calibration data preferably includes a relationship of the amount of total polar material of the frying oil in the vessel and/or the amount of free fatty acids in the vessel as a function of permittivity of the frying oil, in particular at a certain oil temperature, and optionally as a function of the type of frying oil. The relationship may be a mathematical function or a look-up table. The calibration data, in particular relating to total polar materials, may be created by measurement using a capacitive sensor. Alternatively, or additionally, the calibration data, in particular relating to free fatty acids, may be created by measurement using test strips or FTIR.

According to a preferred embodiment of the invention, the fryer comprises a temperature sensor for measuring the temperature of the frying oil in the frying vessel, in particular in the pump chamber, wherein the analysis unit is configured to determine the amount of total polar material of the frying oil in the vessel and/or the amount of free fatty acids in the frying oil in the vessel additionally depending on the measured temperature of the frying oil. In the method according to the invention it is preferred that a temperature sensor of the fryer measures the temperature of the frying oil in the frying vessel and the analysis unit determines the amount of total polar material of the frying oil in the vessel and/or the amount of free fatty acids in the frying oil in the vessel additionally depending on the measured temperature of the frying oil. The calibration data may depend on temperature. Thus, the calibration data preferably includes a relationship of the amount of total polar material of the frying oil in the vessel and/or the amount of free fatty acids in the vessel as a function of permittivity of the frying oil and as a function of temperature, and optionally as a function of the type of frying oil.

According to a preferred embodiment of the invention, the analysis unit is configured to determine an amount of foreign matter in the frying vessel, in particular cleaning liquid or water, depending on the determined permittivity. In the method according to the invention, it is preferred that the analysis unit determines an amount of foreign matter in the frying vessel, in particular cleaning liquid or water, depending on the determined permittivity. Thereby, residues of cleaning agents and/or water may be detected in the frying vessel and/or in the frying oil. Depending on the amount of foreign matter in the frying vessel operation of the fryer may be controlled and/or stopped.

According to a preferred embodiment of the invention, the fryer, the food processing line, a centralized control system and/or the guided wave radar sensor comprises a memory unit configured to store a temporal course of the permittivity and/or the amount of total polar material and/or the amount of free fatty acids. The method according to the invention preferably includes that a temporal course of the permittivity and/or the amount of total polar material and/or the amount of free fatty acids is stored. The temporal course of the permittivity and/or the amount of total polar material and/or the amount of free fatty acids may be stored in a logfile, preferable a logfile for each batch of food products to be fried. The logfile may be kept for the purpose of quality control.

According to a preferred embodiment of the invention, the analysis unit is configured to determine a filling level of the frying oil in the frying vessel and/or in a storage tank that is arranged in fluid communication with the frying vessel based on measurements of the respective guided wave radar sensor. In the method according to the invention, it is preferred that the analysis unit determines a filling level of the frying oil in the frying vessel and/or storage tank based on measurements of the respective guided wave radar sensor. The filling level can be determined by measuring the reflection of a signal at the surface of the frying oil, that is the air-oil interface. The analysis unit may calculate the distance between the transmitter and the surface of the frying oil based on the measured time of flight of the reflected signal.

According to a preferred embodiment of the invention, the analysis unit is configured to generate a warning if the permittivity exceeds a predetermined threshold and/or if the amount of total polar material exceeds a predetermined threshold and/or if the amount of free fatty acids exceeds a predetermined threshold. In the method according to the invention, it is preferred that a warning is generated if the permittivity exceeds a predetermined threshold and/or the amount of total polar material exceeds a predetermined threshold and/or the amount of free fatty acids exceeds a predetermined threshold. The threshold may, e.g., be in the range of 20% to 22% of total polar materials. The warning can be perceived by a user of the machine, e.g., a machine supervisor who may exchange the frying oil or may add replacement frying oil to the vessel and/or the storage tank of the fryer.

According to a preferred embodiment of the invention, the fryer and/or the food processing line comprises a control unit that is configured to control

- an inflow of replacement frying oil into the frying vessel, preferably from a storage tank that is arranged in fluid communication with the frying vessel; and/or
- an outflow of used frying oil from the frying vessel, preferably to a storage tank that is arranged in fluid communication with the frying vessel based on the measurements of the guided wave radar sensor.

In the method according to the invention it is preferred that

- an inflow of replacement frying oil into the frying vessel, preferably from a storage tank that is arranged in fluid communication with the frying vessel; and/or
- an outflow of used frying oil from the frying vessel, preferably to a storage tank that is arranged in fluid communication with the frying vessel is controlled based on the measurements of the guided wave radar sensor.

The replacement frying oil may be fresh frying oil or frying oil satisfying certain maximum requirements regarding permittivity and/or total polar materials and/or free fatty acids. Thereby, frying oil quality in the fryer may automatically be adjusted to a predetermined quality range. For example, the fryer may automatically add replacement frying oil to the vessel from storage tank in case the analysis unit finds that frying oil quality has dropped below a predetermined threshold, e.g., if the amount of total polar materials exceeds a predetermined threshold.

According to a preferred embodiment of the invention, the analysis unit is configured to predict an end of frying oil lifetime at which the permittivity and/or the amount of total polar material and/or the amount of free fatty acids will exceed a predetermined threshold. In the inventive method it is preferred that an end of frying oil lifetime is predicted at which the permittivity and/or the amount of total polar material and/or the amount of free fatty acids will exceed a predetermined threshold. With the predicted end of frying oil lifetime, it is possible to plan ahead exchanging the frying oil and/or refreshing the frying oil, e.g., by adding replacement frying oil to the frying oil in the frying vessel.

According to a preferred embodiment of the invention, the analysis unit is configured to generate a warning based on the measurements of the guided wave radar sensor if the predicted end of lifetime falls within a predetermined time window for processing a batch of products. In the inventive method it is preferred that a warning is generated based on the measurements of the guided wave radar sensor if the predicted end of lifetime falls within a predetermined time window for processing a batch of products. The warning may indicate that it will be required to exchange the frying oil or refresh the frying oil before end of the current batch of food products to be processed.

These and other aspects of the invention will be apparent from and elucidated with reference to the embodiments described hereinafter.

DETAILED DESCRIPTION

Figures 1A, 1B:
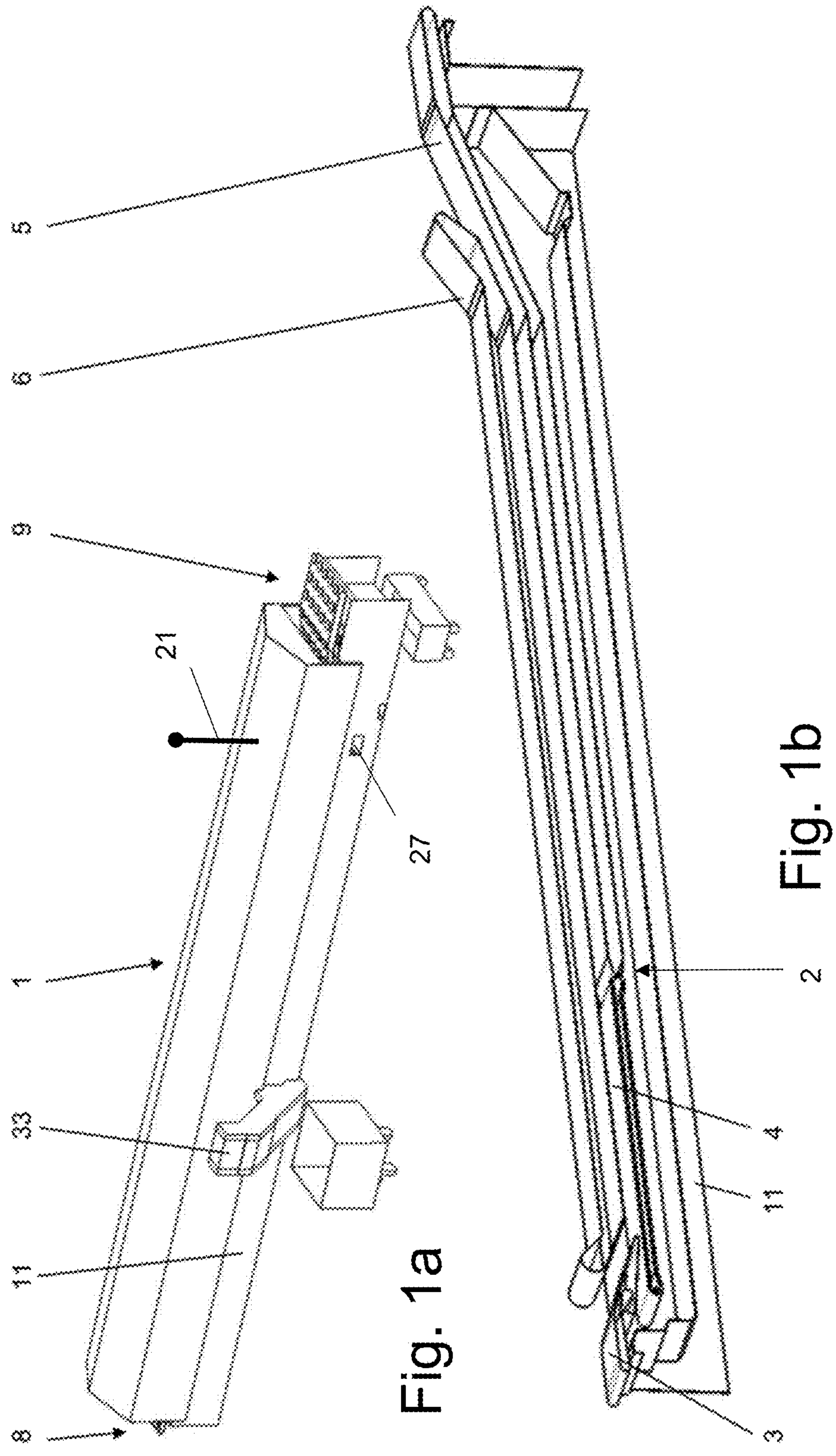
FIG. 1*a* depicts a fryer according to an embodiment of the invention in a perspective view.
FIG. 1*b* depicts the interior of the fryer shown in FIG. 1*a;*

FIGS. 1*a* and 1*b* illustrate a fryer 1 according to an embodiment of the invention. The fryer 1 is configured as an industry-scale fryer for continuous operation. It comprises a frying vessel 11 and a main conveyor 2 for conveying food products to be fried through the frying vessel 11. The fryer 1 includes a product entry 8 through which the food products enter the fryer 1 during regular operation. On a side opposing the product entry 8, the fryer 1 has a product exit 9 through which food products leave the fryer 1 after having been fried. The main conveyor 2 of the fryer 1 is configured for conveying food products from the product entry 8 to the product exit 9. The main conveyer 4 comprises at least one belt 4, 5, which is implemented as an endless mesh belt. According to the embodiment, the main conveyer 2 includes two belts 4, 5. The fryer 1 may additionally comprise a submerge conveyor 6 that hinders the products from floating to the frying oil surface. The submerge conveyor 6 also has a belt, in particular an endless mesh belt. The submerge conveyor 6 is arranged above the main conveyor 2. The fryer 1 further includes a dirt removal device 33. For controlling operation of the fryer 1, the fryer 1 comprises a control system 27. Alternatively, or additionally, the fryer 1 may be controlled by a control system of a food processing line including the fryer 1 and/or a centralized control system.

In order to determine the quality of the frying oil in the frying vessel 11 the fryer 1 comprises a guided wave radar sensor 21 for determining a permittivity of the frying oil 10 accommodated in the frying vessel 11 based on measurement data of the guided wave radar sensor 21. Based on the permittivity, the quality of the frying oil 10 in the frying vessel 11 may be determined. The guided wave radar sensor 21 further enables in-line real-time determination of frying oil quality, whereby the processing of food products in the industrial scale fryer 1 is improved in case an oil management is enabled.

The fryer 1 according to the embodiment further comprises a temperature sensor 15 for measuring the temperature of the frying oil 10 in the frying vessel 11. The temperature sensor 15 may be submerged in the frying oil 10.

In the fryer 1 according to the depicted embodiment, the guided wave radar sensor 21 is arranged in the frying vessel 11. However, additionally or alternatively a guided wave radar sensor 21 may be arranged in a storage tank 28 (depicted in FIG. 5) for holding the frying oil which storage tank 28 is fluidly connected to the frying vessel 11.

Figure 2:
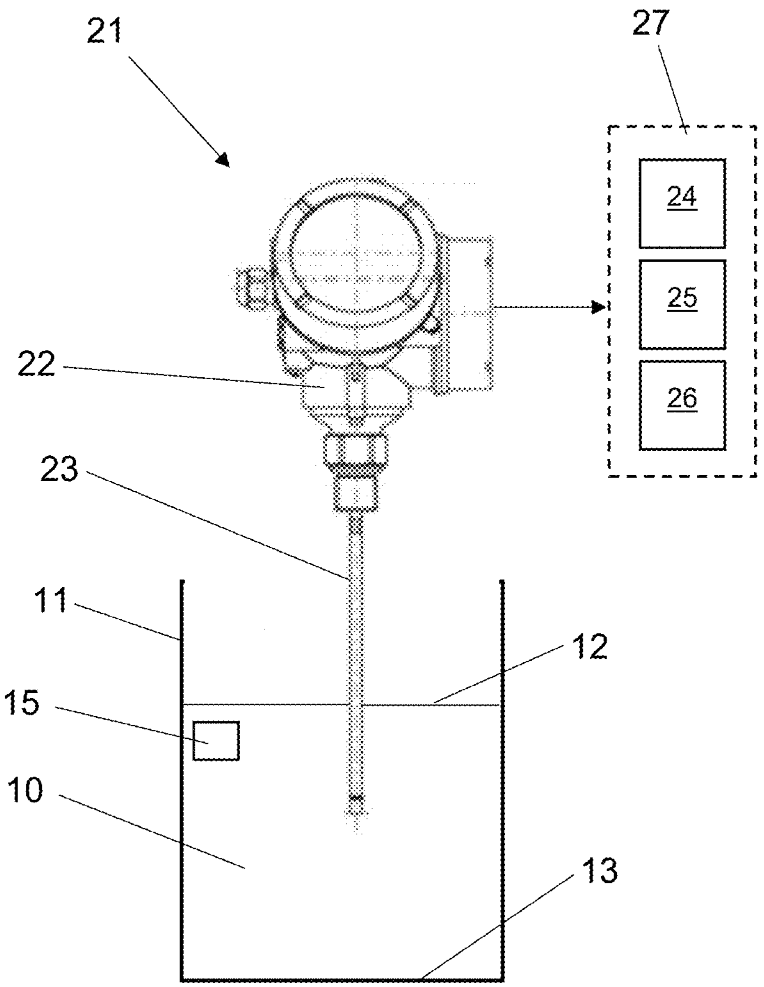
FIG. 2 depicts a guided wave radar sensor for use in the fryer according to FIG. 1*a;*

As indicated in FIG. 2, the control system 27 of the fryer 1 comprises an analysis unit 24, a control unit 25 and a memory unit 26. The analysis unit 24 of the fryer 1 is configured to determine a permittivity of the frying oil 10 in the vessel 11. Then, the analysis unit 24 determines an amount of total polar material of the frying oil 10 in the vessel 11 and/or an amount of free fatty acids in the frying oil 10 in the vessel 11 based on the determined permittivity and the measured temperature. As the permittivity of frying oil changes during use of the frying oil, measuring the permittivity is a reliable method of determining total polar materials. Together with knowledge about the type of frying oil in the frying vessel 11 it is possible to determine the amount of free fatty acids based on the determined permittivity. The analysis unit 24 uses predetermined calibration data which includes a relationship of the amount of total polar material TPM of the frying oil in the vessel and/or the amount of free fatty acids FFA in the vessel as a function of permittivity of the frying oil and/or temperature, and optionally as a function of the type of frying oil.

The temporal course of the determined values, here the temporal course of the permittivity and/or the amount of total polar material and/or the amount of free fatty acids may be determined and stored in the memory unit 26.

The guided wave radar sensor 21 further enables determining the filling level of the frying oil 10 in the frying vessel 11 and in case a guided wave radar sensor 21 is applied in storage tank 28 also in storage tank 28. Based on the determined filling level, the analysis unit 24 may calculate the amount of frying oil absorbed by the food products.

During operation of the fryer 1, the analysis unit 24 may generate a warning if the permittivity exceeds a predetermined threshold and/or if the amount of total polar material exceeds a predetermined threshold and/or if the amount of free fatty acids exceeds a predetermined threshold. In case a guided wave radar sensor 21 is arranged in the storage tank 28 the warning may be generated with respect to the content of the storage tank 28.

The analysis unit 24 may predict an end of frying oil lifetime at which the permittivity and/or the amount of total polar material and/or the amount of free fatty acids will exceed a predetermined threshold. Then, the analysis unit 24 may generate a warning based on the measurements of the guided wave radar sensor 21 if the predicted end of lifetime falls within a predetermined time window for processing a batch of products. In case a guided wave radar sensor 21 is arranged in the storage tank 28 the warning may be generated with respect to the content of the storage tank 28.

Additionally, or alternatively, the control unit 25 may control an inflow of replacement frying oil into the frying vessel 11 from the storage tank 28 and/or an outflow of used frying oil 10 from the frying vessel 11 to the storage tank 28 based on the measurements of the guided wave radar sensor 21.

The guided wave radar sensor 21 will be described with reference to FIG. 2 which depicts an embodiment of a guided wave radar sensor 21 to be employed in a fryer 1 according to the invention.

The guided wave radar sensor 21 comprises a radar transmitter for generating a signal, a waveguide 23 coupled to the radar transmitter for guiding the wave towards and/or through the frying oil 10 and/or a radar receiver for receiving waves reflected by the frying oil 10. In the guided wave radar sensor 21 depicted in FIG. 2, both the transmitter and the receiver are arranged in a common housing 22. The waveguide 23 has the form of a rod or a rope and is partially arranged within the frying oil 10. Here, the free end of the guided wave radar sensor 21, in particular the waveguide 23 of the guided wave radar sensor 21, is submerged in the frying oil 10.

The guided wave radar sensor 21 is configured to measure time of flight of signals sent by the transmitter over the waveguide 23 and received by the receiver after being reflected by the oil surface 12.

Figure 3:
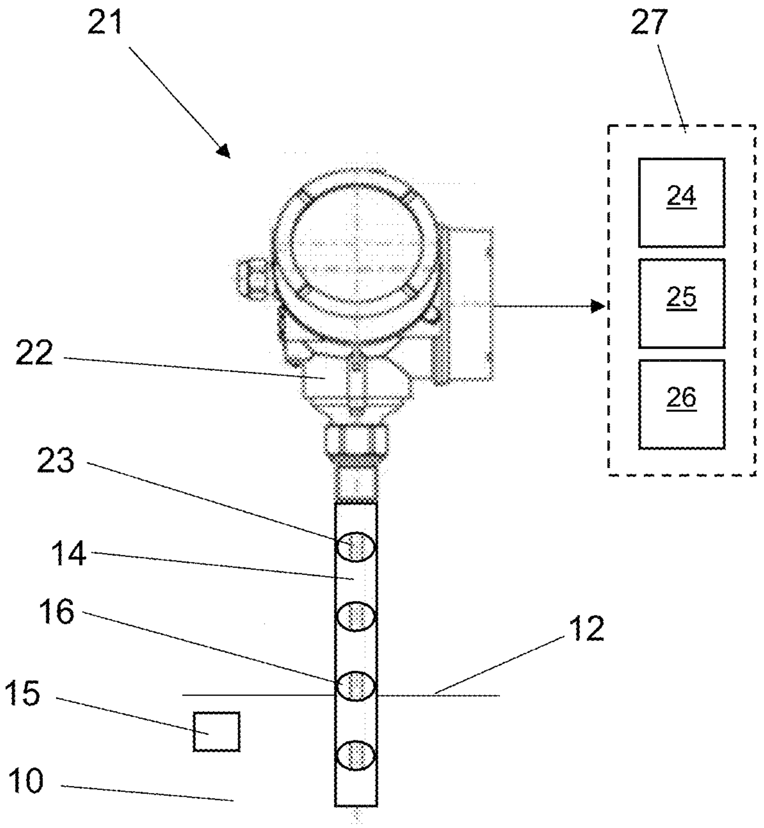
FIG. 3 depicts another guided wave radar sensor for use in the fryer according to FIG. 1*a;*

FIG. 3 depicts an alternative embodiment of a guided wave radar sensor 21 that may be used in the fryer according to the invention. The guided wave radar sensor 21 is similar to the one shown in FIG. 2. In contrast to the guided wave sensor of FIG. 2, the guided wave sensor 21 according to FIG. 3 includes a stilling well 14. The stilling well 14 is arranged coaxial with the waveguide 23. The free end of the stilling well 14 is submerged in the frying oil 10, that means the lower end of the stilling well 14 is located below the air-oil interface 12. The stilling well 14 comprises multiple openings 16 through which frying oil 10 may flow from the outside of the stilling well 14 to the inside, and vice versa. The openings are arranged in a shell surface of the stilling well 14.

Figure 4:
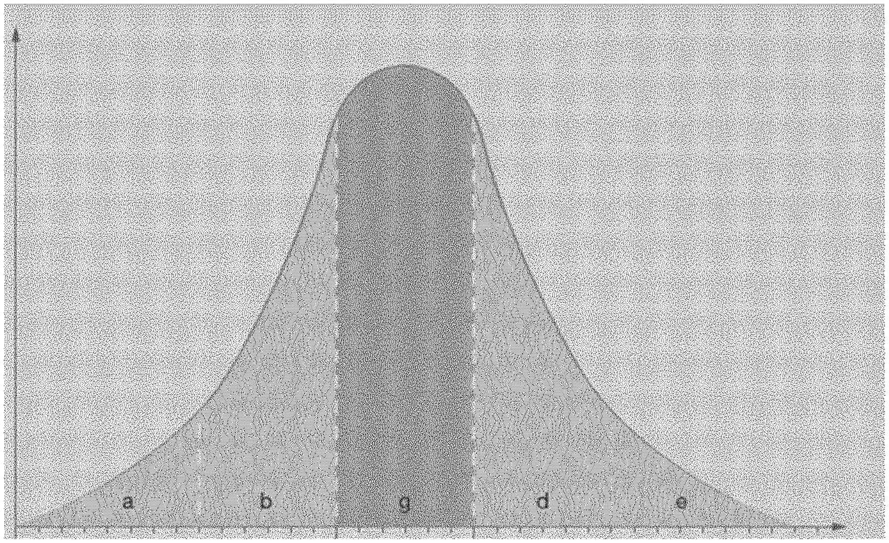
FIG. 4 depicts a frying oil quality diagram.

FIG. 4 depicts a frying oil quality diagram. The quality of the frying oil can be classified in five stages:

stage a: Break In (typically 0% to 8% TPM)
stage b: fresh (typically 8% to 14% TPM)
stage g: optimum (typically 14% to 22% TPM)
stage d: degrading (typically from 22% to 24% TPM)
stage e: runaway (typically above 24% TPM)

Figure 5:
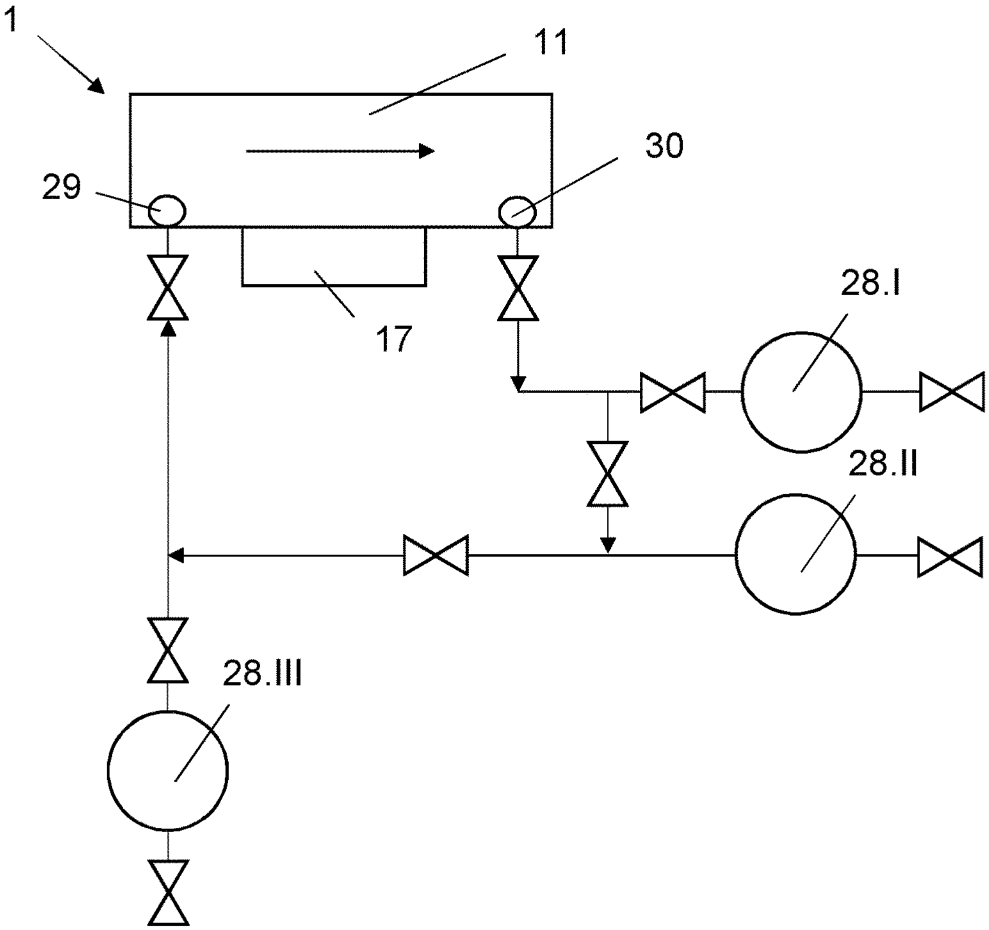
FIG. 5 depicts a setup comprising a fryer according to an embodiment of the invention and connected storage tanks.

FIG. 5 depicts an embodiment with multiple storage tanks 28 which are fluidly connected to fryer 1. It is commonly that the fryer vessel 11 and/or pump chamber 17 comprises inflow opening 29 for the supply of replacement oil and outflow opening 30 for oil which will be discharged from fryer 1. In the depicted embodiment inflow oil will be derived from storage tank 28.III (replacement oil; for instance, fresh frying oil) and/or storage tank 28.II (replacement oil; for instance, oil satisfying certain maximum requirements regarding permittivity and/or total polar materials and/or free fatty acids). Outflow oil will flow towards storage tank 28.I (used oil; for instance contaminated oil which no longer can be used) and/or storage tank 28.II (replacement oil; oil satisfying certain maximum requirements regarding permittivity and/or total polar materials and/or free fatty acids). The number/capacity of fryers and the intended oil management will determine the number of storage tanks to be used. Valves and pumps will be used in order to manage the oil flows. What will be managed is the level of the oil in the fryer (for instance replacement oil has to be added due to the pickup of oil by the food products) and/or the storage tank(s) and the quality of oil (permittivity/TPM/FFA)

In the fryer 1 according to the invention, the predetermined threshold for the amount of total polar material is mainly depended by the type of product (for instance the taste, colour) the customer wants to produce, by the local regulations, etcetera and will typically be set to a value in the range of 14% to 26%, preferably 16%-24%, more preferably 20-22%, so that the fryer 1 will operate using frying oil 10 with optimum quality.

In practice the situation can arise that oil from storage tank 28.I (used oil; for instance contaminated oil which no longer can be used) will be reused in combination with oil from storage tank 28.II (replacement oil; for instance, oil satisfying certain maximum requirements regarding permittivity and/or total polar materials and/or free fatty acids) and/or with oil from storage tank 28.III (replacement oil; for instance, fresh frying oil). A reason for doing this can be to achieve a certain taste and colour (somewhat darker colour) of the fried food products. From importance is that in all cases the oil used during frying is within the requirements regarding permittivity and total polar materials and free fatty acids.

If the predetermined threshold is exceeded, replacement frying oil will be fed into inflow opening 29 within frying vessel 11 from storage tank 28.II and/or 28.III after used frying oil 10 is drained through outflow opening 30 from frying vessel 11 to storage tank 28.I and/or 28.II in order to lower the amount of total polar materials in the frying oil 10 and/or to empty the fryer for instance while the fryer need to be cleaned.

LIST OF REFERENCE SIGNS

1 fryer
2 main conveyor
3 infeed conveyor
4 belt
5 belt
6 submerge conveyor
8 food product entry
9 food product exit
10 frying oil
11 frying vessel
12 air-oil-interface
13 bottom
14 stilling well
15 temperature sensor
16 opening
17 pump chamber
21 guided wave radar sensor
22 housing
23 waveguide
24 analysis unit
25 control unit
26 memory unit
27 control system
28,28I-III storage tank
29 oil inflow opening
30 oil outflow opening
33 dirt removal device

The invention claimed is:

1. A fryer for frying food products comprising:
a frying vessel for accommodating a frying oil,
a guided wave radar sensor arranged in the frying vessel, and
an analysis unit for determining a permittivity of the frying oil in the frying vessel based on measurement data of the guided wave radar sensor,
wherein the fryer is configured for continuously frying food products and comprises at least one conveyor for conveying the food products to be fried through the frying vessel.

2. The fryer according to claim 1, wherein the analysis unit is configured to determine the permittivity of the frying oil in the frying vessel based on the measurement data of the guided wave radar sensor associated with a signal reflection at an interface between air and the frying oil.

3. The fryer according to claim 1, wherein the analysis unit is configured to determine an amount of foreign matter in the frying vessel or cleaning liquid or water, depending on the determined permittivity.

4. The fryer according to claim 1, wherein a memory unit is configured to store a temporal course of the permittivity and/or an amount of total polar material and/or an amount of free fatty acids.

5. The fryer according to claim 1, wherein the analysis unit is configured to determine a filling level of the frying oil in the frying vessel and/or in a storage tank that is arranged in fluid communication with the frying vessel based on measurements of the guided wave radar sensor.

6. The fryer according to claim 1, wherein the analysis unit is configured to generate a warning if the permittivity exceeds a predetermined threshold and/or if an amount of total polar material exceeds a predetermined threshold and/or if an amount of free fatty acids exceeds a predetermined threshold.

7. The fryer according to claim 1, wherein the analysis unit is configured to predict an end of frying oil lifetime at which the permittivity will exceed a predetermined threshold.

8. The fryer according to claim 7, wherein the analysis unit is configured to generate a warning based on the measurements of the guided wave radar sensor if the predicted end of the frying oil lifetime falls within a predetermined time window for processing a batch of food products.

9. The fryer according to claim 1, wherein the guided wave radar sensor comprises a stilling well.

10. A food processing line comprising the fryer according to claim 1.

11. A fryer for frying food products comprising:

a frying vessel for accommodating a frying oil, a guided wave radar sensor arranged in the frying vessel, and an analysis unit for determining a permittivity of the frying oil in the frying vessel based on measurement data of the guided wave radar sensor, wherein the analysis unit is configured to determine an amount of total polar material of the frying oil in the frying vessel and/or an amount of free fatty acids in the frying oil in the frying vessel depending on the determined permittivity.

12. The fryer according to claim 11, wherein the analysis unit is configured to determine the amount of total polar material of the frying oil in the frying vessel and/or the amount of free fatty acids in the frying oil in the frying vessel additionally depending on predetermined calibration data.

13. A fryer for frying food products comprising:

a frying vessel for accommodating a frying oil, a guided wave radar sensor arranged in the frying vessel, and an analysis unit for determining a permittivity of the frying oil in the frying vessel based on measurement data of the guided wave radar sensor, wherein the analysis unit is configured to determine an amount of total polar material of the frying oil in the frying vessel and/or an amount of free fatty acids in the frying oil in the frying vessel depending on the determined permittivity, and wherein the fryer comprises a temperature sensor for measuring a temperature of the frying oil in the frying vessel or in a pump chamber, wherein the analysis unit is configured to determine the amount of total polar material of the frying oil in the frying vessel and/or the amount of free fatty acids in the frying oil in the frying vessel additionally depending on the measured temperature of the frying oil.

14. A fryer for frying food products comprising:

a frying vessel for accommodating a frying oil, a guided wave radar sensor arranged in the frying vessel, an analysis unit for determining a permittivity of the frying oil in the frying vessel based on measurement data of the guided wave radar sensor, a control unit that is configured to control an inflow of replacement frying oil into the frying vessel or from a storage tank that is arranged in fluid communication with the frying vessel and/or an outflow of used frying oil from the frying vessel or to the storage tank that is arranged in fluid communication with the frying vessel, based on the measurements of the guided wave radar sensor.

15. A method for frying food products in a frying vessel of a fryer, the frying vessel contains frying oil or melted frying fat, wherein the method comprises:

conveying with at least one conveyor the food products to be fried through the frying vessel, and determining with an analysis unit a permittivity of the frying oil accommodated in the frying vessel based on measurement data of a guided wave radar sensor, wherein the guided wave radar sensor is arranged in the frying vessel.

* * * * *